United States Patent
Penzel et al.

(10) Patent No.: US 7,928,270 B2
(45) Date of Patent: Apr. 19, 2011

(54) PROCESS FOR DISTILLATIVELY REMOVING DINITROTOLUENE FROM PROCESS WASTEWATER FROM THE PREPARATION OF DINITROTOLUENE BY NITRATING OF TOLUENE WITH NITRATING ACID

(75) Inventors: Ulrich Penzel, Tettau (DE); Ruediger Fritz, Strassgraebchen (DE); Holger Allardt, Schwarzheide (DE); Johannes Adam, Dresden (DE); Anne-Kathrin Merten, Lauchhammer (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 309 days.

(21) Appl. No.: 12/280,176

(22) PCT Filed: Mar. 6, 2007

(86) PCT No.: PCT/EP2007/052072
§ 371 (c)(1),
(2), (4) Date: Aug. 21, 2008

(87) PCT Pub. No.: WO2007/101844
PCT Pub. Date: Sep. 13, 2007

(65) Prior Publication Data
US 2009/0043135 A1    Feb. 12, 2009

(30) Foreign Application Priority Data

Mar. 7, 2006   (EP) ..................................... 06110748

(51) Int. Cl.
*C07C 205/00* (2006.01)
(52) U.S. Cl. ......... 568/934; 568/927; 568/939; 568/940
(58) Field of Classification Search .................. 568/927, 568/934, 939, 940
See application file for complete search history.

(56) References Cited

U.S. PATENT DOCUMENTS

| 6,506,948 | B1 | 1/2003 | Sawicki | |
|---|---|---|---|---|
| 2004/0262238 | A1* | 12/2004 | Munnig et al. | 210/749 |

FOREIGN PATENT DOCUMENTS

| DE | 101 43 800 | 8/2002 |
|---|---|---|
| DE | 103 56 499 | 6/2005 |
| EP | 0 953 546 | 11/1999 |
| WO | 97 38770 | 10/1997 |

* cited by examiner

*Primary Examiner* — Jafar Parsa
(74) *Attorney, Agent, or Firm* — Oblon, Spivak, McClelland, Maier & Neustadt, L.L.P.

(57) ABSTRACT

A process is proposed for distillatively removing dinitrotoluene from process wastewater from the preparation of dinitrotoluene by nitrating toluene with nitrating acid, which comprises
  basifying the process wastewater to a pH of >8.5,
  feeding it to a stripping column in the upper region thereof and
  stripping it with steam in countercurrent to obtain
    a vapor stream laden with dinitrotoluene and
    a bottom stream depleted in dinitrotoluene compared to the process wastewater used.

16 Claims, No Drawings

PROCESS FOR DISTILLATIVELY REMOVING DINITROTOLUENE FROM PROCESS WASTEWATER FROM THE PREPARATION OF DINITROTOLUENE BY NITRATING OF TOLUENE WITH NITRATING ACID

The invention relates to a process for distillatively removing dinitrotoluene (DNT) from process wastewaters which are obtained in the preparation of DNT by nitrating toluene with nitrating acid. In the abovementioned process for preparing DNT, various process wastewaters are obtained, i.e. aqueous streams which cannot be utilized further in the process or whose utilization is uneconomic, and which are fed to wastewater treatment. For this treatment, strict limiting values with regard to permissible residual concentrations of chemical compounds are prescribed; for example, especially the limiting values for nitroaromatics are very low, since they are biodegradable only with difficulty.

Various processes have therefore been developed in order to reduce both the amount of the process wastewater obtained in the process for preparing DNT and its loading with chemical substances, especially with organic substances.

DE-B 103 56 499 describes a process for rectificative subazeotropic concentration of aqueous NOx-containing diluted waste and mixed acids which are generally obtained in plants with nitric acid consumption, but especially in washing processes in nitrating plants, and which comprise essentially nitric acid, sulfuric acid, water and organics in subazeotropic composition. The aqueous waste acids are subjected to rectification without changing the pH thereof, i.e. as are obtained in the plant with nitric acid consumption, thus with a pH in the acidic range. Although the process enables a removal of a portion of the nitroorganics, especially mononitrotoluene (MNT) and DNT via the top stream of the rectification column, as performed in the examples, this is a depletion to about only half of the nitroorganics burden compared to the aqueous waste acid stream fed to the rectification, in particular from about 2.0% by weight to about 1.0% by weight.

U.S. Pat. No. 6,506,948 describes a process for treating wastewaters from the preparation of DNT by reacting toluene with nitric acid and sulfuric acid, toluene being used as the extractant for MNT and DNT. Disadvantages here are that an additional circuit is required for the toluene extractant, the process requires increased energy consumption for workup of the extractant, and safety problems which entail explosion-proof design of the entire plant.

DE 101 43 800 describes a process for reducing the amount of wastewater obtained in the preparation of DNT, according to which the process wastewater obtained in the sulfuric acid concentration is first freed of undissolved MNT and DNT gravimetrically, i.e. by phase separation on the basis of the density differences of aqueous and organic phase, the process wastewater thus prepurified is neutralized and the MNT is subsequently removed therefrom by stripping with steam, after which the process wastewater thus purified can be recycled into the plant by scrubbing the DNT. A disadvantage is that, under the process conditions described (steam stripping of pH-neutral process wastewater), the DNT is removed only in a small fraction and remains in the process wastewater (paragraph [0016] from DE-C 101 43 800) and thus considerably disrupts the long-term stable operation of the downstream wastewater treatment.

WO 97/38770 describes the distillation of wastewaters comprising DNT in the presence of nitric acid (25-60%). The vapor stream is virtually free of DNT (<50 ppm by weight) and the DNT fed into the distillation remains in the bottom effluent, which greatly impairs the long-term stable operation of the downstream wastewater treatment.

It was accordingly an object of the invention to provide a process by which the DNT content in process wastewaters from the preparation of DNT can be reduced substantially by reacting toluene with nitric acid in a simple manner without use of additional organic auxiliary streams. The lifetime of downstream wastewater treatment plants should be increased and the chemical oxygen demand in the water treatment plant, based on this wastewater stream, should be reduced.

The solution consists in a process for distillatively removing dinitrotoluene from process wastewater from the preparation of dinitrotoluene by nitrating toluene with nitrating acid, which comprises
  basifying the process wastewater to a pH of >8.5,
  feeding it to a stripping column in the upper region thereof and
  stripping it with steam in countercurrent to obtain
    a vapor stream laden with dinitrotoluene and
    a bottom stream depleted in dinitrotoluene compared to the process wastewater used.

It has been found that it is possible to substantially remove DNT from process wastewaters from the preparation of DNT by reacting toluene with nitrating acid by steam stripping, by basifying the pH of the process wastewater before feeding it to the steam stripping.

DNT is generally prepared in a continuous process by nitrating toluene with nitrating acid, a mixture of sulfuric acid and nitric acid, to obtain MNT in a first process step and DNT in a second process step. In addition to the main DNT product, by-products formed are especially nitrocresols. DNT is removed by the sulfuric acid diluted with water of reaction and subjected to multistage scrubbing with dilute nitric acid, sodium carbonate solution and water. The alkaline wastewater from the DNT scrubbing, which in particular still comprises MNT, DNT and nitrocresols and has a pH of >8.5, is a first process wastewater stream which can be subjected to the inventive depletion by steam stripping, and will be referred to below as stream 1.

The sulfuric acid diluted with water of reaction, which is obtained in the nitration and has a concentration of approx. 71% by weight, is concentrated by heating, generally in several stages, in particular to up to approx. 90% by weight in a first stage and up to approx. 94% by weight in a second stage in order to be able to be recycled again into the nitration of toluene. The process wastewaters obtained in the concentration of the approx. 71% by weight sulfuric acid are referred to below as stream 2. Stream 2 can be fed to the process according to the invention for depleting DNT, basified to a pH of >8.5, either separately or combined with stream 1.

Moreover, nitric acid is supplied as a 65% solution in many plants, because it is known that it can be transported in equipment of low-alloy steel without corroding it. This nitric acid must, in order to be able to be used in the process for nitrating toluene, be concentrated to about 98%, generally by rectification with sulfuric acid as a water-binding compound. The process wastewater obtained here is referred to below as stream 3 and can likewise be subjected to the inventive steam stripping together with stream 1 and/or stream 2, or else fed directly to biological wastewater treatment.

Stream 1 and/or stream 2 and/or stream 3 are heated, especially to boiling temperature, i.e. in the region of about 100° C. at standard pressure, preferably by means of heating steam in one or more stages, and fed in the upper region of a distillation column which is used as a stripping column.

The process wastewater is preferably heated to a temperature in the range from 60 to 120° C. before being fed to the stripping column.

The stripping column is preferably operated continuously. Advantageously, customary separating internals, structured packings or especially random packings are introduced in the stripping column.

In the lower region of the stripping column, stripping steam is raised by means of a bottoms circulation evaporator and/or stripping is effected with externally supplied steam. This can preferably be drawn from the typically available low-pressure steam line system.

The amount of steam used, based on the dinitrotoluene burden of the process wastewater fed to the stripping column, is preferably in the range from 20 to 1000 kg of steam per kg of dinitrotoluene, in particular of between 100 and 600 kg of steam per kg of dinitrotoluene.

In addition, a small amount of preheated inert gas, especially nitrogen, may be introduced in the lower region of the stripping column in order to support the stable operation of the column.

The stripping column is preferably operated at a top pressure in the range from 500 to 3000 mbar absolute, especially under standard pressure.

From the stripping column, a vapor stream comprising DNT-laden steam is drawn off and can preferably be condensed in a condenser at the top of the column and separated in a phase separator into an organic and an aqueous phase. The organic (heavier) phase is preferably recycled into the process for preparing DNT. The aqueous (lighter) phase is preferably fed partly back to the stripping column as reflux and otherwise preferably recycled into the process for preparing DNT, in particular to the DNT scrubbing.

When the phase separation is dispensed with, the condensed vapor stream which is not recycled as reflux into the column is preferably recycled into the DNT scrubbing.

The bottom stream drawn off is DNT-depleted wastewater which is preferably depleted further of fractions of organic impurities still present therein by treating it by oxidative wastewater pretreatment methods, for example ozonolysis, treatment with hydrogen peroxide/iron sulfate, thermolysis. The wastewater from the oxidative wastewater pretreatment is sent to biological wastewater treatment.

The process according to the invention allows a depletion of DNT from wastewaters from DNT preparation of up to 90% to be achieved, in particular from a starting loading of the process wastewater feed stream fed to the stripping column of from about 400 to 3000 ppm by weight of DNT to a residual content of the bottom stream drawn off from the stripping column of from 20 to 300 ppm by weight of DNT. This is especially surprising since the equilibrium concentration of DNT in water is known to be low, and is below 1% by weight.

The hydroxyl-bearing aromatic nitro compounds remain entirely in the bottoms and are virtually fully degraded in the downstream oxidative wastewater pretreatment stage.

The invention will be illustrated in detail with reference to a working example. Process wastewater from the industrial scale plant for preparing DNT by means of toluene and having a residual DNT content of 900 ppm by weight was fed continuously to a laboratory column with a diameter of 60 mm, which was filled with random packings, in the upper region thereof. The process wastewater fed to the stripping column was basified to a pH of 9.4. The stripping column had two theoretical plates. 1.3 kg/h of 0.5 bar steam were introduced in countercurrent in the lower region of the stripping column. The stripping column was operated at atmospheric pressure and top temperature approx. 100° C. At a feed of 2.1 kg/h of wastewater, 64 ppm by weight of DNT isomers remained in the bottom effluent.

The experiment shows that a depletion of DNT of over 90% is possible by stripping with steam.

What is claimed is:

1. A process for distillatively removing dinitrotoluene from process wastewater from the preparation of dinitrotoluene by nitrating toluene with nitrating acid, which comprises
   basifying the process wastewater to a pH of >8.5,
   feeding it to a stripping column in the upper region thereof and
   stripping it with steam in countercurrent to obtain
      a vapor stream laden with dinitrotoluene and
      a bottom stream depleted in dinitrotoluene compared to the process wastewater used.

2. The process according to claim 1, wherein the process wastewater is adjusted to a temperature in the range from 60 to 120° C. before it is fed to the stripping column.

3. The process according to claim 1, wherein the stripping column is operated continuously.

4. The process according to claim 1, wherein the steam is raised by means of a bottoms circulation evaporator and/or supplied externally.

5. The process according to claim 1, wherein the amount of steam used, based on the dinitrotoluene burden of the process wastewater fed to the stripping column, is in the range from 20 to 1000 kg of steam per kg of dinitrotoluene.

6. The process according to claim 1, wherein the process wastewater fed to the stripping column, before it is fed to the stripping column, is preheated.

7. The process according to claim 1, wherein the stripping column is operated at a top pressure in the range from 500 to 3000 mbar absolute.

8. The process according to claim 1, wherein inert gas is fed to the stripping column in the lower region thereof.

9. The process according to claim 1, wherein the vapor stream from the stripping column is condensed and subsequently introduced into a phase separator in which it is separated into an organic phase which is recycled into the process for preparing dinitrotoluene, and into an aqueous phase which is introduced partly as reflux back to the stripping column.

10. The process according to claim 1, wherein the bottom product from the stripping column is fed to a process stage for oxidative treatment of the fractions of organic substances still present therein.

11. The process according to claim 1, wherein process wastewater with a content of dinitrotoluene in the range from 400 to 3000 ppm by weight is fed to the distillative removal in the stripping column and a bottom stream with a content of dinitrotoluene in the range from 20 to 300 ppm by weight is drawn off from the stripping column.

12. The process according to claim 5, wherein the amount of steam used, based on the dinitrotoluene burden of the process wastewater fed to the stripping column, is in the range between 100 and 600 kg of steam per kg of dinitrotoluene.

13. The process according to claim 6, wherein the process wastewater fed to the stripping column, before it is fed to the stripping column, is preheated to boiling temperature.

14. The process according to claim 6, wherein the process wastewater fed to the stripping column, before it is fed to the stripping column, is preheated with heating steam.

15. The process according to claim 9, wherein the vapor steam from the stripping column is condensed and subsequently introduced into a phase separator in which it is separated into an organic phase which is recycled into the process for preparing dinitrotoluene, and into an aqueous phase which is introduced partly as reflux back to the stripping column and is otherwise recycled into the process for preparing dinitrotoluene.

16. A process for distillatively removing dinitrotoluene from a process wastewater formed during the preparation of dinitrotoluene by nitrating toluene with a nitrating acid, comprising:
 basifying the process wastewater to a pH of >8.5 to form a basified waste water, then
 feeding the basified process wastewater to an upper region of a stripping column, and then
 stripping the basified process wastewater with steam in countercurrent to obtain:
  a vapor stream comprising dinitrotoluene, and
  a bottom stream depleted in dinitrotoluene, wherein the bottom stream comprises an amount of dinitrotoluene that is less than the amount of dinitrotoluene in the process wastewater subjected to the basifying.

\* \* \* \* \*